(12) United States Patent
Kasai et al.

(10) Patent No.: US 7,238,355 B1
(45) Date of Patent: Jul. 3, 2007

(54) COATED MATERIAL AND PROCESS FOR PRODUCING THE COATED MATERIAL

(75) Inventors: Takahide Kasai, Takasaki (JP); Takahiro Eguchi, Takasaki (JP); Kimiko Takai, Takasaki (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/514,312

(22) Filed: Feb. 28, 2000

(30) Foreign Application Priority Data

Feb. 26, 1999 (JP) ............... 11-050291

(51) Int. Cl.
*A61K 35/84* (2006.01)

(52) U.S. Cl. .................... 424/195.16

(58) Field of Classification Search ........ 424/464, 424/465, 468, 470, 474, 475, 479, 489, 490, 424/493, 499, 195.1, 491, 498; 514/54
See application file for complete search history.

(56) References Cited

U.S. PATENT DOCUMENTS

| | | | | |
|---|---|---|---|---|
| 4,001,480 A | * | 1/1977 | Shank | 428/411 |
| 4,774,093 A | * | 9/1988 | Provonchee et al. | 424/493 |
| 4,962,094 A | * | 10/1990 | Jamas et al. | 514/54 |
| 5,521,089 A | * | 5/1996 | Ishiguro et al. | 435/255.2 |
| 6,020,324 A | * | 2/2000 | Jamas et al. | 514/54 |
| 6,444,448 B1 | * | 9/2002 | Wheatcroft et al. | 435/101 |

FOREIGN PATENT DOCUMENTS

| | | |
|---|---|---|
| JP | 53-18773 | 2/1978 |
| JP | 53-45385 | 4/1978 |
| JP | 56-011791 | 2/1981 |
| JP | 56-19971 | 5/1981 |
| JP | 04-117245 | 4/1992 |
| JP | 4-248968 | 9/1992 |
| JP | 9-103266 | 4/1997 |

* cited by examiner

*Primary Examiner*—Humera N Sheikh
*Assistant Examiner*—Hasan S. Ahmed
(74) *Attorney, Agent, or Firm*—Venable LLP; Nancy J. Axelrod; Robert Kinberg

(57) ABSTRACT

A coated material and a process for producing the coated material which includes providing a coating agent comprising yeast cell wall fractions, as a primary constituent, consisting of cell residue of yeast which has been treated with enzymes, optionally subsequently with acidic solution, and water to remove internal soluble cell constituents; and coating a solid material with the coating agent to provide a coating thereon.

12 Claims, 4 Drawing Sheets

COATED MATERIAL AND PROCESS FOR PRODUCING THE COATED MATERIAL

BACKGROUND OF THE INVENTION

1. Field of the Invention

The present invention relates to a coating agent which is safe to use, which can be coated even in 100% water, which affords a finish that is not sticky despite its viscosity, thus resulting in coated particles that do not stick to each other, and which has an extremely low oxygen permeation coefficient, as well as to a novel, edible coating agent consisting of yeast cell wall fractions with the function of controlling dissolution time, coated materials comprising the use of such coating agents, and a coating film formed from such a coating agent.

2. Description of the Related Art

Fine particles, microcapsules, granules, tablets, and the like, comprising useful coated substances in a variety of forms or with various properties, such as colorless or colored dyes, medicinal products, agrochemicals, fragrances, feed materials, and food product materials, have conventionally been prepared for industrial purposes. Known examples of bases for coating fragrances, feed materials, food product materials, and the like, specifically, coating agents, include waxes and other oils, natural polysaccharides, proteins, shellac (natural resin secreted by the lac insect living in plants such as the legumes) and other resins, and the like. Chemically synthesized coating bases stipulated for medicinal additives are also known in the case of medicinal products.

Most of such conventionally known coating agents, however, suffer from the drawback of poor handling as a result of stickiness or poor dispersion during the preparation of the coating liquid. Additional problems with most medicinal additives such as shellac, zein (corn protein), and ethylcellulose, are their bad effects on the environment and their high cost because of the use of solvents such as ethanol have been indicated. Although water dispersion types of ethylcellulose-based coating agents have become commercially available recently, these also suffer from problems in terms of handling, such as the changes in solution properties depending on temperature conditions during storage, and the inability to release them in wastewater into rivers because they contain various solvents. Still another problem is the poor intestinal dissolution and the extremely slow dissolution speed of the aforementioned zein which can be used in the field of food products.

Attempts have meanwhile been made to develop film materials from yeast. Japanese Patent Publication (Kokoku) S56-19971, for example, discloses an edible protein film based on water-soluble proteins produced by removing the yeast cell membrane components from residual yeast which was produced by extracting nucleic acid. Japanese Laid-Open Patent Application (Kokai) S53-45385 discloses a method for producing a film, wherein the cells of a microorganism such as yeast are heated and alkali treated, acid is added for treatment involving isoelectric precipitation, the pH of the resulting precipitate is adjusted to between 6 and 8, and a plasticizer is added to the resulting gel-forming microorganism cells to produce a constituent.

Methods are also known for decoloring and deodorizing substances primarily comprising the cell walls left over in the form of residue during the extraction of yeast extract. Japanese Laid-Open Patent Application (Kokai) H4-248968, for example, discloses a method for decoloring and deodorizing yeast extract residue, wherein extract residue is treated with alkali and acid, is then treated with 1000 to 2000 ppm ozone, and is treated with ethanol before and after the ozone treatment. Japanese Laid-Open Patent Application (Kokai) H9-103266 discloses a method for eliminating the flavor and odor of a yeast autolytic insoluble substance, wherein a yeast autolytic insoluble substance is suspended in ethanol, and is stirred and treated in the presence of an alkali.

However, it has not been known that excellent use as a coating agent can be made, without additional chemical treatment, of yeast cell wall fractions consisting of yeast extract residue, for example, such as extract residue obtained after the components in soluble cells have been removed following the autolysis of live yeast cream at 40 to 50° C., or that further treatment of such yeast cell wall fractions with acidic aqueous solution affords a coating agent with better enteric properties allowing the time at which dissolution begins to be controlled.

That is, an object of the present invention is to provide a coating agent with an extremely low oxygen permeation coefficient, which remedies the drawbacks of conventional edible coating agents, for example, by having a finish that is not as sticky, despite its viscosity, as gums such as gum arabic, resins such as shellac, and zein or Eudragit, and which results in coated particles that do not stick to each other, as well as to a coating agent which can be used as an enteric coating agent capable of controlling the time at which dissolution begins.

In the course of research on yeast cell wall fractions occurring in the form of extract residue of yeast extract, particularly in the course of research on coating agents utilizing such yeast cell wall fractions, the inventors unexpectedly found that residue undergoing no ethanol treatment as described in Japanese Laid-Open Patent Applications H4-248968 or H9-103266, or any other chemical treatment during the treatment of the yeast extract residue had better film-formability, that is, film-forming properties, than that which had been treated with ethanol, and were particularly better as coating agents which require film properties, and that yeast cell wall fractions without any chemical treatment can be used as an unexpectedly excellent coating agent. Upon further research on such yeast cell wall fractions, the present invention was perfected when it was discovered that an excellent enteric coating agent capable of controlling the time at which dissolution begins was unexpectedly obtained using only acidic aqueous solution in varying concentrations, unlike conventional conditions for treating yeast with both alkali and acid treatments for deodorization and decolorization.

SUMMARY OF THE INVENTION

That is, the present invention relates to a coating agent, characterized in which the primary component of which comprises yeast cell wall fractions consisting of cell residue obtained by removing the internal soluble cell components of enzyme-treated yeast; a coating agent, characterized in which the primary component of which comprises acid-treated yeast cell wall fractions consisting of cell residue obtained by removing the internal soluble cell components of enzyme-treated yeast, the aforementioned residue being treated with an acidic aqueous solution to further remove solubilized components; the aforementioned coating agents which is characterized by further comprising a plasticizer; a coated material, comprising a material coated with the aforementioned coating agents; the aforementioned coated material, characterized in which the coated material comprises a granular material such as fine particles, granules, or tablets; the aforementioned coated material, characterized in which the coated material comprises food products, food product materials, medicinal preparations, enzymes, microorganisms, seeds, agrochemicals, fertilizer, fragrances, or pigments; a coating film formed by any of the aforementioned coating agents; and the aforementioned coating film, further comprising a plasticizer.

DESCRIPTION OF THE PREFERRED EMBODIMENTS

Starting Material Yeast

Figure 1:
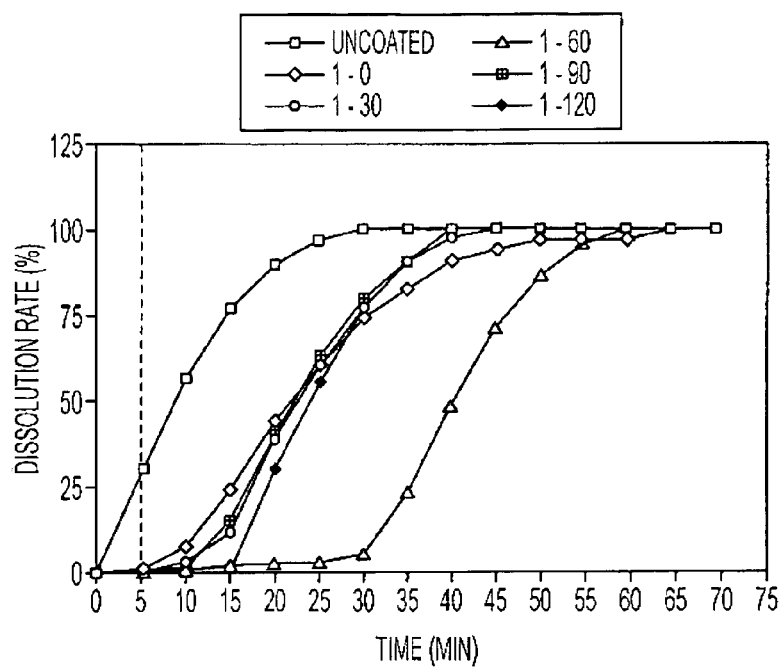
FIG. 1 gives the measured results in dissolving tests with water using coating agents of which the primary component comprising the yeast cell wall fractions of the present invention.

Any yeast taxonomically belonging to yeasts may be used as the yeast serving as the starting material for the coating agent of the present invention. Examples include brewer's yeast, wine yeast and baker's yeast. More specific examples include *Saccharomyces cerevisiae, Saccharomyces rouxii, Saccharomyces carlsbergensis, Candida utilis, Candida tropicalis, Candida lipolytica*, and *Candida flaveri.*

Such yeasts can be used alone or in combination. The use of live yeast is preferred, although yeasts in configurations other than live yeast such as dried yeast can also be used, and can, for example, be treated in the same manner as live yeast by being suspended in water or the like. The size or configuration of the yeast that is used is not particularly limited, although the configuration is preferably as close as possible to spherical, and the size preferably ranges from between 1 and 20 µm.

Yeast Cell Wall Fractions

Yeasts contain water- or polar solvent-soluble internal cell components such as proteins, amino acids, saccharides, nucleic acids, and organic acids. Such internal cell components are readily solubilized in water, and when used as a coating agent without the removal of such soluble internal cell components, not only is the effect of delaying the time at which for dissolution begins inhibited, but the coating strength is also compromised. It is thus necessary to use yeast cell wall fractions obtained by removing the soluble internal cell components from yeast in order to obtain a coating agent with an effective time delay before dissolution begins.

To obtain yeast cell wall fractions by removing such soluble internal cell components from the yeast, it is necessary to solubilize such internal cell components by enzyme treatment to remove them from the cells. Any enzyme treatment used during the production of yeast internal cell components in the form of yeast extract can be used as the enzyme treatment, such as so-called autolysis featuring the use of the enzymes inside yeast cells; methods for adding enzymes, in which external enzymes such as proteases, nucleases, β-glucanase, esterases, and lipases are added; or combinations of such methods. This allows effective use to be made of the extract residue of yeast extract in the manufacture of common yeast extract, in the form of the yeast cell wall fractions in the present invention. To speed up or the like, the enzyme treatment, pretreatment for physically rupturing the cell walls with a high pressure homogenizer or the like may be carried out before the enzyme treatment of the yeast. When such a high pressure homogenizer is used, the material is preferably dispersed at a pressure of between 100 and 1,000 kg/cm$^2$, for example.

At the completion of the enzyme treatment, the yeast is treated to remove the soluble internal cell components, such as by centrifugation, to obtain yeast cell wall fractions in the form of cell residue. The yeast cell wall fractions thus obtained without any particular chemical treatment consist of a film that is relatively durable in physical and chemical terms, consisting of glucan, mannan, and chitin layers, and can thus be used as an excellent coating agent capable of encapsulating greater amounts of substances without compromising the function of protecting the encapsulated substances. However, the yeast cell wall fractions can also be prepared with the incorporation of yeast washing treatments, adjustment of the pH, temperature, or pressure, and the like as needed.

Acid-Treated Yeast Cell Wall Fractions

The acid-treated yeast cell wall fractions can be prepared in the form of yeast cell residue by treating the yeast with an enzyme treatment to remove the soluble internal cell components, and treating the resulting yeast cell wall fractions with an acidic aqueous solution to then further remove the solubilized components. More specifically, the aforementioned yeast cell wall fractions can be treated with 0.01 to 2 N, and preferably 0.1 to 0.5 N, acid such as hydrochloric acid, sulfuric acid, or nitric acid, the resulting suspension can be centrifuged or the like to separate the supernatant and yeast cell residue, and the yeast cell residue can be harvested to prepare the acid-treated yeast cell wall fractions. The material is also preferably heated to around 80° C. during the acid treatment.

The resulting acid-treated yeast cell wall fractions consist of a film that is relatively durable in physical and chemical terms, consisting of glucan, mannan, and chitin layers, and can thus be used as an excellent enteric coating agent or the like that is capable of encapsulating greater amounts of a substance without compromising the function of protecting the encapsulated substance, and that also allows the time at which dissolution begins to be controlled by changing the concentration of the acidic water that is used.

Coating Agent

Coating agents in the present invention which are based on yeast cell wall fractions or are based on acid-treated yeast cell wall fraction include, in addition to coating agents consisting of these yeast cell wall fractions and acid-treated yeast cell wall fractions, coating agents comprising the addition of adjuvants as needed to these yeast cell wall fractions and acid-treated yeast cell wall fractions. These yeast cell wall fractions and acid-treated yeast cell wall fractions can be used as such to obtain excellent coating agents, but it is sometimes desirable to use an adjuvant such as a plasticizer to enhance the spreading properties, water resistance, or the like of the coating film. Examples of such additives, in the field of food products, include glycerin, sorbitol, amino acids, organic acids, monoglycerides, diglycerides, triglycerides, and MCT-based oils, which can be used specifically as plasticizers. Examples in the field of pharmaceutical products include triacetin, triethyl citrate, acetylated monoglycerides, and any other plasticizer given in lists of pharmaceutical adjuvants.

Physical Properties of Coating Agents

The coating agents of the present invention have excellent properties allowing them to be used as bitterness masking agents or enteric coating agents which, compared to conventional edible coating agents, have a nonsticky finish despite their viscosity, resulting in coated particles that do not stick together, and which are capable of controlling the time at which dissolution begins. Coating layers (films) comprising the coating agents of the present invention have an extremely low oxygen or other gas permeability and moisture permeability, and are better than existing edible films, making them suitable for use in a wide range of fields, such as food products, pharmaceutical products, feed, agrochemicals, and the like. Conventional coating agent solutions involve the use of quasi viscous fluids of dissolved polymers or dilatant fluid such as aqueous suspensions of starch, but the coating agents of the present invention are plastic fluids, and have different physical properties than conventional types.

Encapsulated Substances

Any substance that is a solid at ordinary temperature can be used as the encapsulated substance coated by the coating agent of the present invention. Examples include food products, food product materials, enzymes, microorganisms, pharmaceutical products, seeds, agrochemicals, fertilizer, fragrances, and pigments. Examples of the aforementioned food products and food product materials include starch food products, tableted food products, Western style confectioneries (candies, sweets, chocolate, chewing gum, etc.), Japanese style confectioneries (such as crackers), baked confectioneries (such as castella, cookies, and crackers), gummy candies, fried snacks (such as potato chips, snacks, and the like), various sauces, soy sauce, miso sauce, mayonnaise, or dressings in the form of powders or solids, various beverages (such as fruit juices, nectars, carbonated beverages, sports beverages, teas, coffee, cocoa, soups, and alcoholic beverages) in the form of powders or solids, various powder extracts (meats such as beef, pork, or chicken, seafood such as shrimps, scallops, corbicula, kelp and any marine products, vegetables and fruits, plants, yeast, etc.), oils and flavoring (vanilla, citrus, bonito, etc.) in the form of powders or solids, powder spices and herbs (red pepper, black pepper, Japanese sansho pepper, yuzu citron, basil, and the like), powdered beverages (such as instant coffee, instant tea, instant milk, instant soups and miso soups, etc.), various dairy products (such as cheese), various nutrient and nutritional supplement foods materials (such as Vitamins A, B, C, D, and E, Edible microorganism of *Bifidobacterium, Lactobacillus, Clostridium butyricum* and other useful bacteria, *chlorella*, calcium and magnesium minerals, propolis, and the like), sprinkles, flakes, toppings (such as croutons), processed soy (such as tofu and bean curd dregs) in the form of solids, fresh and processed foods (such as curry and stews) in the form of solids and frozen foods (plain and coated), and various processed food products. The coating agents of the present invention are suitable for use when the encapsulated substance is in granulated form, such as fine particles, granules, or tablets, or when the encapsulated substance itself is in a form resembling granules, such as seeds. Such encapsulated substances can be coated with the coating agent of the present invention to obtain the coated material of the present invention. Further, the coating agent of the present invention can also be used to produce a film without coating an encapsulated substance in order to obtain the coating film of the present invention, which has an extremely low oxygen permeation coefficient or moisture permeation coefficient.

Coating Process

The aforementioned encapsulated substances can be coated with the coating agent of the present invention by producing the aforementioned encapsulated substances, either individually or in combination, in the form of granulated products having a suitable diameter, such as fine particles, granules, or tablets, and coating them with the coating agent of the present invention suspended in water or a mixture of water and solvent. Specifically, a coating device such as the Doria Coater (by Powrex Co., Ltd), for example, can be used to spray coat the substance to be encapsulated with a suspension of the coating agent of the present invention, although any well-known coating method or device can be used.

The drying temperature during the coating process, that is, the drying temperature after the encapsulated substance has been coated with the suspension of the coating agent of the present invention, is not particularly limited, although the substance should ordinarily be dried at a temperature of between 60 and 90° C. The drying temperature can be set according to the temperature stability of the encapsulated substance. Additionally, the drying time can be extended to obtain effects similar to the curing effects of latex-type coating agents used in pharmaceutical adjuvants. And the amount of coating agent is determined according to the amount of the encapsulated substance that is used, the intended application, and the like.

EXAMPLES

The present invention is described in further detail below with reference to examples, but the technical scope of the present invention is not limited to these examples. The amounts of the yeast cells given in the examples are actual weight (dry weight).

Example 1

Brewer's yeast slurry by-product was procured from a beer plant and was centrifuged for 10 minutes at 4500 rpm, and the resulting slushy live yeast was suspended in water to a solids concentration of 5 wt %. The suspension was allowed to undergo autolysis for 17 hours at 50° C., the product was centrifuged again to remove the soluble internal cell components, and the resulting autolysis residue was used as the yeast cell wall fraction. Then the yeast cell wall fraction was dispersed in water to a solids concentration of 10 wt %, and glycerin was dispersed as a plasticizer to 15 wt % of the yeast cell wall fraction solids, so as to prepare a coating liquid.

As the encapsulated substance, tablets consisting of 3.6 mg acetaminophen, 112.8 mg lactose, 3.0 mg HPC-L, and 0.6 mg magnesium stearate (total of 120 mg/tablet) were formed in advance, and these tablets were spray coated with the coating liquid using a Doria Coater (Powrex Co., Ltd) to a tablet:coating agent ratio of 80:20 (weight ratio), giving Samples 1. The resulting Samples 1 were shelf dried for 0, 30, 60, 90, and 120 minutes at 80° C., giving Samples 1-0, 1-30, 1-60, 1-90, and 1-120.

These samples 1-0, 1-30, 1-60, 1-90, and 1-120, and an uncoated control (no coating) were tested in dissolution tests (paddle method) based on the Japan Pharmacopoeia. 500 mL of 37° C. water was used as the solvent in the dissolution tests with each type of sample tablet to determine the dissolution rate based on acetaminophen absorption (Abs 242). The results are given in FIG. 1. FIG. 1 reveals that all of the samples had slower dissolution than the uncoated control, thus confirming the coating effects. It may thus be concluded that the present coating agent is suitable for precoating bitterness masking agents or sugar-coated tablets.

Example 2

Samples were prepared in the same manner as in Example 1 except that torula yeast was used instead of the brewer's yeast used in Example 1. The same dissolution test (paddle method) based on the Japan Pharmacopoeia revealed results similar to those for Sample 1 in Example 1.

Example 3

Brewer's yeast slurry by-product was procured from a beer plant and was centrifuged for 10 minutes at 4500 rpm, and the resulting slushy live yeast was suspended in water to a solids concentration of 5 wt %. 10,000 U of Zymoliase 20T (Seikagaku Kogyo) was added to 500 g of the suspension and allowed to act thereon for 8 hours at 37° C., the mixture was centrifuged again to remove the soluble internal cell components, and the resulting autolysis residue was used as the yeast cell wall fraction. The yeast cell wall fraction was then treated in the same manner as in Example 1 to prepare samples. The same dissolution test (paddle method) based on the Japan Pharmacopoeia revealed results similar to those for Sample 1 in Example 1.

Example 4

Yeast cell wall fractions obtained in the form of autolysis yeast residue in Example 1 were suspended in 0.1 N hydrochloric acid to a solids concentration of 5%, treated with acid for 20 minutes at 80° C., and then centrifuged for 15 minutes at 4500 rpm to remove the solubilized components, and the resulting residue was used as the acid-treated yeast cell wall fraction. The acid-treated yeast cell wall fraction was then dispersed in water to a solids concentration of 7 wt %, and glycerin was dispersed as a plasticizer to 7 wt % of the yeast cell wall fraction solids, so as to prepare a coating liquid.

The aforementioned tablets prepared in advance were then spray coated with the coating liquid using a Doria Coater (Powrex Co., Ltd) to a tablet:coating agent weight ratio of 90:10, 80:20, 70:30, and 60:40, giving Samples 2, 3, 4, and 5. The resulting Samples 2 through 5 were shelf dried for 0, 30, 60, 90, and 120 minutes at 80° C., giving Samples 2-0, 2-30, 2-60, 2-90, and 2-120, Samples 3-0, 3-30, 3-60, 3-90, and 3-120, Samples 4-0, 4-30, 4-60, 4-90, and 4-120, and Samples 5-0, 5-30, 5-60, 5-90, and 5-120.

Example 5

Samples 6 through 9 were prepared in the same manner as Example 4 except that the concentration of the hydrochloric acid used in Example 4 was changed from 0.1 N to 0.5 N. The resulting Samples 6 through 9 were shelf dried for 0, 30, 60, 90, and 120 minutes at 80° C., giving Samples 6-0, 6-30, 6-60, 6-90, and 6-120, Samples 7-0, 7-30, 7-60, 7-90, and 7-120, Samples 8-0, 8-30, 8-60, 8-90, and 8-120, and Samples 9-0, 9-30, 9-60, 9-90, and 9-120.

Figure 2:
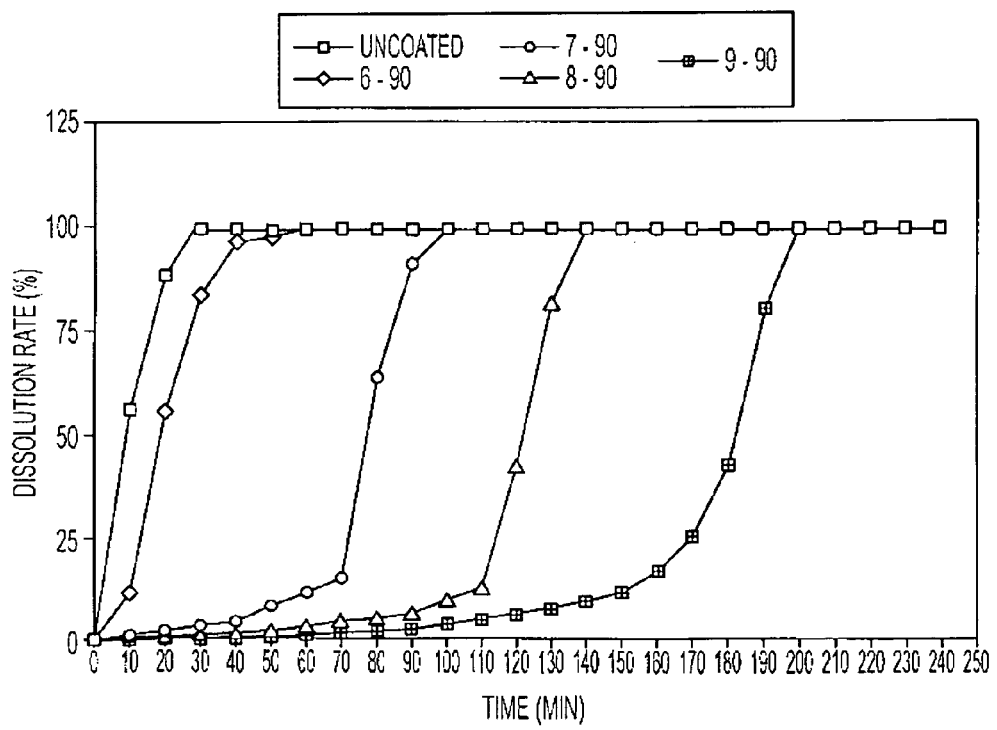
FIG. 2 gives the measured results in dissolving tests with water on varying amounts of coating agents of which the primary component comprising the acid-treated yeast cell wall fractions of the present invention.

Samples 6-90, 7-90, 8-90, 9-90, and an uncoated control (no coating) were tested in dissolution tests (paddle method) based on the Japan Pharmacopoeia. 500 mL of 37° C. water was used as the solvent in the dissolution tests with each type of sample tablet to determine the dissolution rate based on acetaminophen absorption (Abs 242). The results are given in FIG. 2. FIG. 2 reveals that the time at which dissolution began could be controlled according to the amount of coating.

Figure 3:
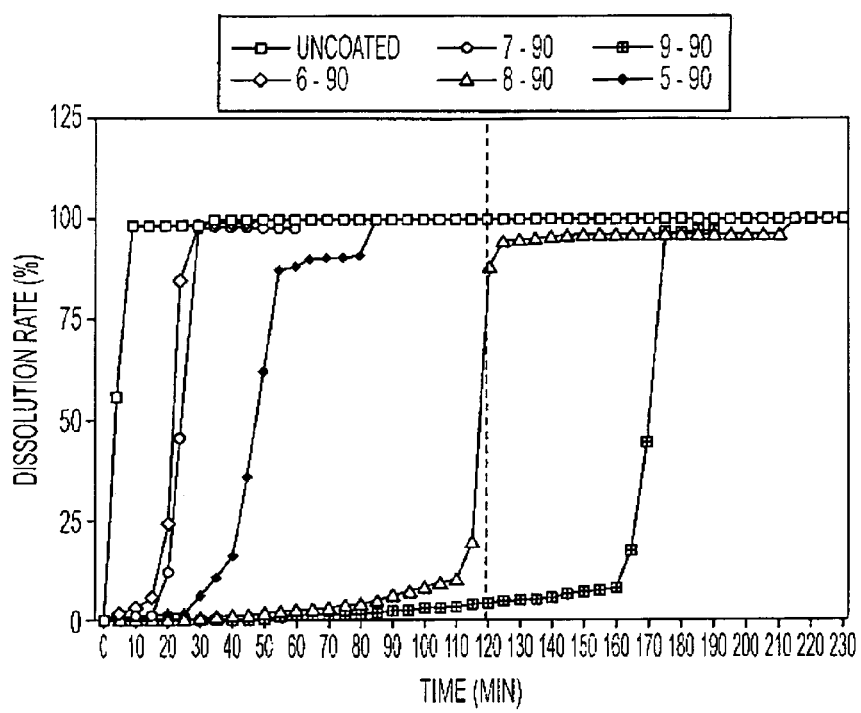
FIG. 3 gives the measured results in dissolution tests with artificial gastric juice on varying amounts of coating agents of which the primary component comprising the acid-treated yeast cell wall fractions of the present invention.

Samples 5-90, 6-90, 7-90, 8-90, 9-90, and an uncoated control (no coating) were tested in dissolution tests (paddle method) based on the Japan Pharmacopoeia. The dissolution solvent was Japan Pharmacopoeia XIII $1^{st}$ fluid (pH1.2), and the dissolution rate was determined for each sample tablet based on acetaminophen absorption (Abs 242) in 500 mL of 37° C. Japan Pharmacopoeia XIII 1st fluid (pH1.2). The results are given in FIG. 3. FIG. 3 reveals that the time at which dissolution began could also be controlled according to the amount of coating in artificial gastric juice. This suggests that the coating agent of the present invention is also useful as an enteric coating agent.

Figure 4:
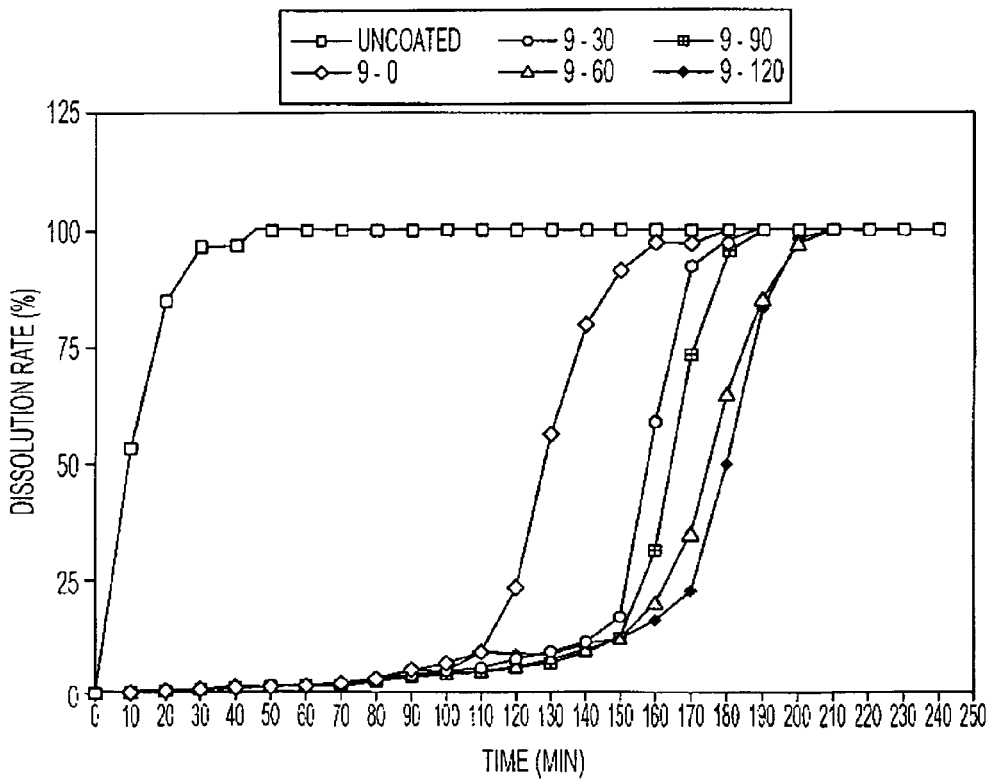
FIG. 4 gives the measured results in dissolution tests with water at varying drying times using coating agents of which the primary component comprising the acid-treated yeast cell wall fractions of the present invention.

Samples 9-0, 9-30, 9-60, 9-90, 9-120, and an uncoated control (no coating) were tested in dissolution tests (paddle method) based on the Japan Pharmacopoeia. 500 mL of 37° C. water was used as the solvent in the dissolution tests with each type of sample tablet to determine the dissolution rate based on acetaminophen absorption (Abs 242). The results are given in FIG. 4. FIG. 4 reveals that the drying time following coating did not have much of an effect on dissolution behavior when water was used as a dissolution solvent for Sample 9.

Figure 5:
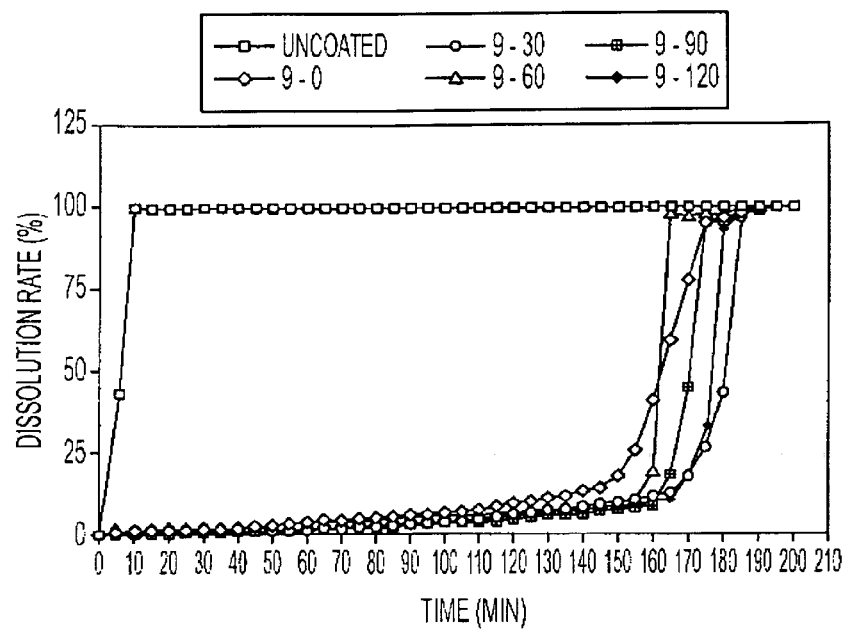
FIG. 5 gives the measured results in dissolution tests with artificial gastric juice at varying drying times using coating agents of which the primary component comprising the acid-treated yeast cell wall fractions of the present invention.

Samples 9-0, 9-30, 9-60, 9-90, 9-120, and an uncoated control (no coating) were tested in dissolution tests (paddle method) based on the Japan Pharmacopoeia. The dissolution solvent was Japan Pharmacopoeia XIII 1st fluid (pH1.2), and the dissolution rate was determined for each sample tablet based on acetaminophen absorption (Abs 242) in 500 mL of 37° C. Japan Pharmacopoeia XIII 1st fluid (pH1.2). The results are given in FIG. 5. FIG. 5 reveals that the drying time following coating did not have much of an effect on dissolution behavior when artificial gastric juice was used as a dissolution solvent for Sample 9.

Figure 6:
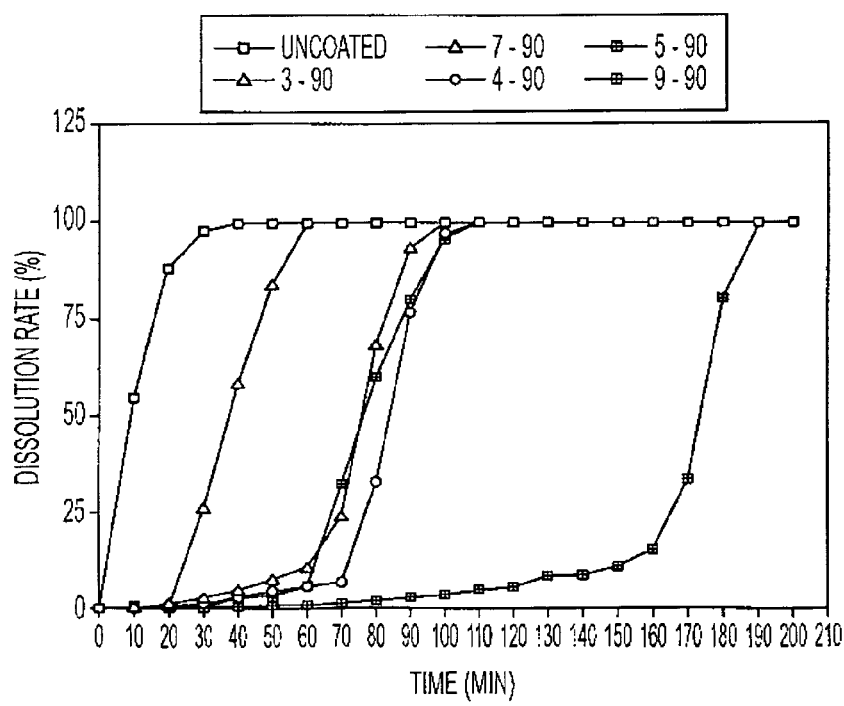
FIG. 6 gives the measured results in dissolution tests with water on coating agents of which the primary component comprising the acid-treated yeast cell wall fractions with different acid concentrations in the present invention.

Samples 3-90, 7-90, 4-90, 5-90, 9-90, and an uncoated control (no coating) were tested in dissolution tests (paddle method) based on the Japan Pharmacopoeia. 500 mL of 37° C. water was used as the solvent in the dissolution tests with each type of sample tablet to determine the dissolution rate based on acetaminophen absorption (Abs 242). The results are given in FIG. 6. FIG. 6 reveals that the time at which dissolution began could be controlled based on the acid treatment conditions. This suggests that the coating agent of the present invention was also useful as an enteric coating agent.

Example 6

Yeast cell wall fractions obtained in the form of autolysis yeast residue in Example 1 were suspended in 0.5 N hydrochloric acid to a solids concentration of 5%, treated with acid for 20 minutes at 80° C., and then centrifuged for 15 minutes at 4500 rpm to remove the solubilized components, resulting in acid-treated yeast cell wall fractions consisting of residue. The acid-treated yeast cell wall fraction yield was 41.4%, and the solids concentration was 9.8 wt %.

Example 7

Samples 10 through 13 were prepared in the same manner as in Example 4, except that the concentration of the hydrochloric acid that was used in Example 4 was changed from 0.1 N to 0.5 N, and the dispersion medium that was used during the preparation of the coating liquid was changed from water to 100% ethanol. These had functions similar to those of Samples 6 through 9. Additionally, since ethanol was used as the dispersion medium when Samples 10 through 13 were used to coat the tablets, it was possible to set the tablet product temperature lower than when Samples 6 through 9 were used to coat the tablets. It was thus evident that the coating agent made lower temperature coating possible.

Example 8

Figure 7:
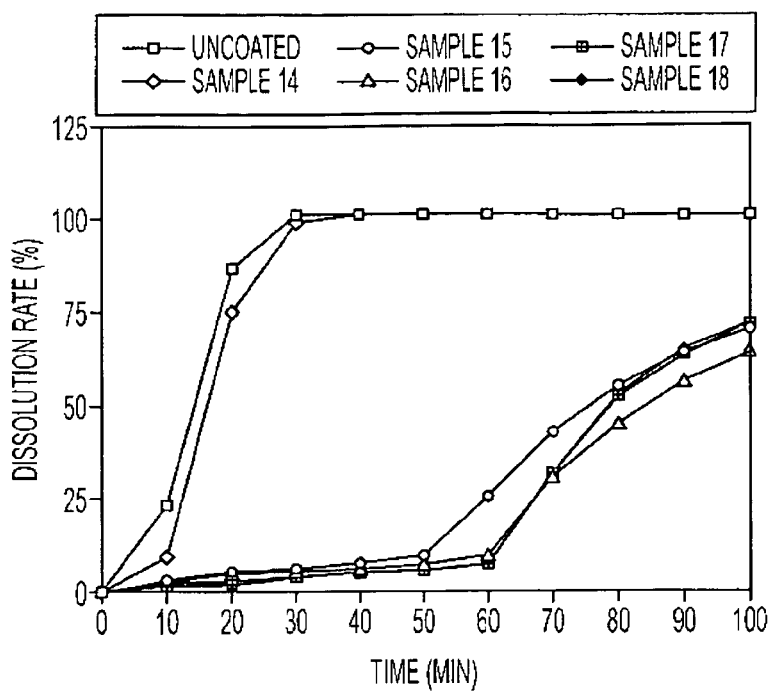
FIG. 7 gives the measured results in dissolution tests with artificial gastric juice at varying drying times using coating agents of which the primary component comprising the acid-treated yeast cell wall fractions of the present invention.

1 g agar and 1.47 g glycerin were added to 20 g acid-treated yeast cell wall fraction prepared by the method described in Example 5, water was then added to bring the total to 400 g, and the ingredients were mixed to homogeneity to prepare a coating liquid. Tablets were then spray coated in the same manner as in Example 4 to a tablet: coating agent ratio of 100:2, 100:4, 100:6, 100:8, and 100:10, giving Samples 14, 15, 16, 17, and 18. These samples and an uncoated control (no coating) were used in dissolution tests (paddle method) based on the Japan Pharmacopoeia. 500 mL of 37° C. Japan Pharmacopoeia XIII 1st fluid (pH1.2) was used as the solvent in the dissolution tests with each type of sample tablet to determine the dissolution rate based on acetaminophen absorption (Abs 242). The results are given in FIG. 7. FIG. 7 reveals that the dissolution rates were similar with an amount of coating agent of 100:6 or more, but with a lag time of 1 hour until dissolution started. This suggests that the encapsulated substance was held by the coating agent, and that the dissolution design could be changed by adding adjuvants.

Example 9

Manufacture of Dried Bonito Granules, and Coating Effects

The granule manufacturing step and coating step involved the use of a Powrex Co., Ltd Multiplex MP-01 model. 135 g of gelatinized corn starch aqueous solution was sprayed onto 528 g of dried bonito meal for granulation to produce dried bonito granules. Yeast cell wall fraction obtained in the form of autolysis yeast residue in Example 1 was then suspended in 0.5 N hydrochloric acid to a solids concentration of 5 wt %, it was treated with acid for 20 minutes at 80° C., and it was then centrifuged for 15 minutes at 4500 rpm to remove the solubilized components, and the resulting residue was used as acid-treated yeast cell wall fractions. The acid-treated yeast cell wall fraction was then dispersed in water to a solids concentration of 5 wt %, and glycerin was dispersed as a plasticizer to 7 wt % of the acid-treated yeast cell wall fraction solids, so as to prepare a coating liquid, which was used to spray coat the dried bonito granules at an air supply temperature of 60° C., an exhaust temperature of 30° C., and a flow rate of 10 g/min. The resulting coated product was clearly more effectively prevented from losing flavor, with the aroma enclosed therein, than uncoated products.

It was possible to coat the material even with the exhaust temperature lowered to 30° C. With shellac, for example, the lowest exhaust temperature was 35° C. under the same conditions, and the lowest temperature was 40° C. with water-based coating agents (such as HPMC). This means that this coating agent can be used to coat granules (food product materials) which are extremely vulnerable to heat, such as chocolate or Edible microorganism of *Bifidobacterium*.

Example 10

Bitterness Masking Effect on Granules

The granule manufacturing step and coating step involved the use of a Powrex Co., Ltd Multiplex MP-01 model. Marker acetaminophen was layered with 50 mesh DMV lactose, and then sorted to a size ranging from 16 to less than 48 mesh to prepare acetaminophen granules. Yeast cell wall fraction obtained in the form of autolysis yeast residue in Example 1 was suspended in 0.5 N hydrochloric acid to a solids concentration of 5 wt %, it was treated with acid for 20 minutes at 80° C., and it was then centrifuged for 15 minutes at 4500 rpm to remove the solubilized components, and the resulting residue was used as acid-treated yeast cell wall fractions. The acid-treated yeast cell wall fraction was then dispersed in water to a solids concentration of 5 wt %, and glycerin was dispersed as a plasticizer to 7 wt % of the acid-treated yeast cell wall fraction solids, so as to prepare a coating liquid. The coating liquid was used to spray coat 500 g acetaminophen granules at an air supply temperature of 60° C., an exhaust temperature of 32° C., and a flow rate of 12 g/min. The granules were coated in amounts of 5, 10, 15, and 20% relative to the granules, giving Samples 19, 20, 21, and 22.

Samples 19, 20, 21, 22 and an uncoated control (plain granules) were tested in dissolution tests (paddle method) based on the Japan Pharmacopoeia. 500 mL of 37° C. water was used as the solvent in the dissolution tests with 50 mg of each type of sample granule based on the uncoated weight to determine the dissolution rate based on acetaminophen absorption (Abs 242). The results are given in FIG. 8.

Figure 8:
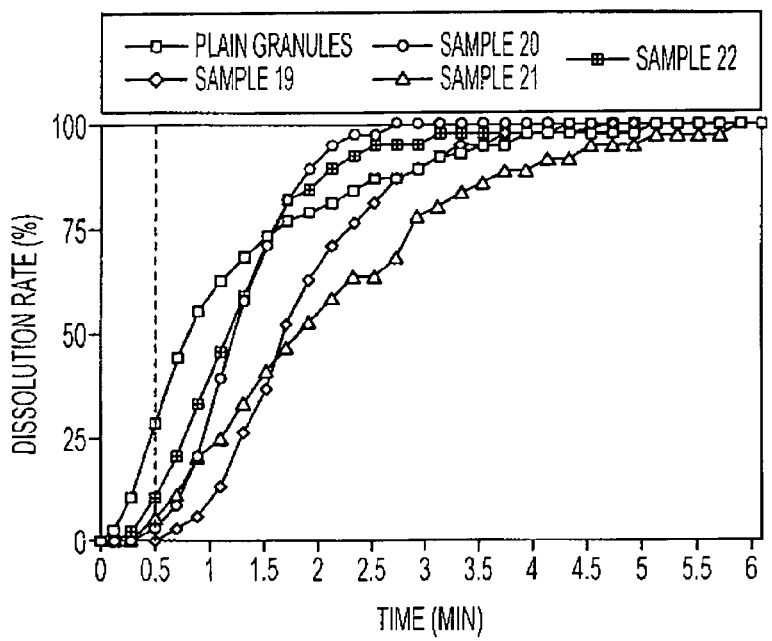
FIG. 8 gives the measured results in dissolution tests with water on granules coated with varying amounts of coating agents in which the primary component comprising the acid-treated yeast cell wall fractions of the present invention.

FIG. 8 reveals no drug dissolution with a 20% coating after 30 seconds. Since a lag time of 30 seconds is generally required until a drug begins to dissolve for the purposes of masking the bitterness of drugs, this example would be effective as a coating agent for masking bitterness. These results are quantitative measurement data, and may be considered more stringent data than organoleptic evaluation by humans.

Example 11

Oxygen Permeation Test

Glycerin as a plasticizer was dispersed in water to 10 wt % of the acid-treated yeast cell fraction solids concentration in a solution with an acid-treated yeast fraction solids concentration of 5 wt % prepared by the method in Example 5, and the ingredients were homogenized to produce a coating liquid. The coating liquid was then introduced into Petri dishes and dried over night at 40° C., resulting in a cast film 0.059 mm thick. An oxygen permeability test was conducted in accordance with JIS K 7126B. The test device was an OX-TRAN 10/50 by Mocon (Modern Controls). The conditions of measurement comprised a temperature of 23° C., 0% humidity, a test surface area of 50 cm$^2$, and an oxygen concentration of 100%.

Example 12

Water Vapor Permeation Test

The coating liquid prepared in Example 11 was used. In the same manner as in Example 11, the coating liquid was introduced into Petri dishes and dried over night at 40° C., resulting in a cast film 0.055 mm thick. A water vapor permeability test was conducted in accordance with JIS Z 0208. The test devices were a hygrothermalstatic chamber PL4SP by Tabaiesupekku Co., Ltd and scales AE200 by Mettler-Toledo Ag. The conditions of measurement comprised a temperature of 40° C., a humidity of 50% RH, and a test surface area of 28.26 cm$^2$. The results revealed a moisture permeability of 322 (g/m$^2$·day·atm) and a moisture permeation coefficient of 17.6 (g·mm/m$^2$·day·atm). These results indicate that the coating film based on the coating agent of the present invention had an extremely low moisture permeation coefficient.

Comparative Example 1

The yeast cell wall fraction obtained in the form of autolysis yeast residue in Example 1 was meanwhile suspended in 0.5 N sodium hydroxide to a solids concentration of 5 wt %, then treated with alkali for 20 minutes at 80° C., and then centrifuged for 15 minutes at 4500 rpm to remove the solubilized components, and the resulting residue was resuspended in 0.5 N hydrochloric acid to a solids concentration of 5 wt %, treated with acid for 20 minutes at 80° C., and centrifuged for 15 minutes at 4500 rpm to remove the solubilized components, giving an alkali- and acid-treated yeast cell wall fraction consisting of the resulting residue. The yield of the alkali- and acid-treated yeast cell wall fraction was 15.8%, and the solids were 7.3 wt %.

The yield of the yeast cell wall fraction in Comparative Example 1 was about as low as 38% of that in Example 6. The combined alkali and acid treatments dramatically lowered the yield compared to that obtained with acid treatment alone. Whereas the acid-treated yeast cell wall fraction of Example 6 had a viscosity of 1 at a solids concentration of 10 wt %, the alkali- and acid-treated yeast cell wall fraction of Comparative Example 1 had a viscosity of 21.9 at a solids concentration of 10 wt %, and because of this high viscosity, coating with the latter took about 1.34 times longer than it did with the former. Furthermore, the alkali- and acid-treated yeast cell wall fraction was heated for a long time in the presence of an alkali, resulting in a greater possibility of producing greater amounts of lysinoalanine, which induces renal cell hypertrophy, making it unsuitable for food products and pharmaceutical products.

Comparative Example 2

500 mL of 100% ethanol was added to 500 g (49 g solids) of acid-treated yeast cell wall fraction slurry prepared in Example 6, the ingredients were stirred for 30 minutes, and the mixture was centrifuged to remove the solubilized fractions, further, 500 mL of 100% ethanol was again added, the ingredients were stirred for 30 minutes, and the mixture was centrifuged to remove the solubilized components, resulting in a residue slurry (acid- and ethanol-treated yeast cell wall fraction). The acid- and ethanol-treated yeast cell wall fraction was then dispersed in water to a solids concentration of 7 wt %, and glycerin was dispersed as a plasticizer to 7 wt % of the acid-treated yeast cell wall fraction solids, so as to prepare a coating liquid. The aforementioned previously prepared tablets were coated with the coating liquid using a Doria Coater (Powrex Co., Ltd) to a tablet:coating agent weight ratio of 90:10, but the film formability was lost compared to samples made using acid-treated yeast cell wall fractions. The surface of the tablets thus became powdery, and this example was concluded to be unsuitable for a coating agent.

The coating agents of the present invention afford the following effects.

(1) Considering its viscosity, the finish is not as sticky as gums such as gum arabic, resins such as shellac, or zein or Eudragit or the like, so that the coated particles do not stick to each other.

(2) The time at which dissolution begins can be controlled according to the amount coated and the acid treatment conditions, allowing the invention also to be used as an enteric coating agent.

(3) The invention is readily dispersed in water, even without the use of emulsifiers or the like, and is capable of coating even in 100% water. It can also be used with a small amount of a solvent mixed therein.

(4) It is also highly safe, since it is not harmful when directly touched and is edible.

(5) It has an extremely low oxygen permeation coefficient, is far better than any existing edible films, and is suitable in a wide range of fields, such as food products, pharmaceutical products, and feed.

What is claimed is:

1. A process for producing a coated material, comprising:
   providing a coating agent comprising yeast cell wall fractions, as a primary constituent, wherein the yeast cell wall fractions consist of cell residue of yeast from which internal soluble cell constituents have been removed by treating yeast cells by autolysis, or with external enzymes selected from the group consisting of proteases, nuclease, β-glucanase, esterases, lipases and combinations thereof, or with a combination of autolysis and one or more of the external enzymes, and subsequently with an acidic aqueous solution followed by a separation step, wherein the yeast have not been treated with alkali; and
   coating the surface of a solid material with the coating agent to form a continuous, low oxygen or gas permeable coating thereon.

2. The process of claim 1, wherein the coating provided on the surface of the solid material is non-sticky and prevents oxygen, other gases, and moisture from permeating the coated material.

3. The process of claim 1, wherein the cell residue of yeast comprises glucan, mannan, and chitin.

4. The process of claim 1, wherein the coating agent further comprises a plasticizer.

5. The process of claim 1, wherein the solid material is selected from the group consisting of fine particles, granules, and tablets.

6. The process of claim 1, wherein the solid material is selected from the group consisting of food products, food product materials, pharmaceuticals, enzymes, microorganisms, seeds, agrochemicals, fertilizers, fragrances, and pigments.

7. A coated material produced by the process according to claim 1.

8. The process of claim 1, further wherein the yeast have been pre-treated to physically rupture the cell walls, then treated by autolysis, or with external enzymes selected from the group consisting of proteases, nuclease, β-glucanase, esterases, lipases and combinations thereof, or with a combination of autolysis and one or more of the external enzymes, and subsequently with an aqueous acidic solution followed by a separation step to remove internal soluble cell constituents.

9. The process of claim 1,
wherein the coating agent consists essentially of cell residue resulting from treating yeast solely by autolysis, or with external enzymes selected from the group consisting of proteases, nuclease, β-glucanase, esterases, lipases and combinations thereof, or with a combination of autolysis and one or more of the external enzymes, and an acidic aqueous solution, followed by a separation step, to remove internal soluble cell constituents.

10. A process for producing a coated material, consisting essentially of:
treating a yeast cell by autolysis, or with external enzymes selected from the group consisting of proteases, nuclease, β-glucanase, esterases, lipases and combinations thereof, or with a combination of autolysis and one or more of the external enzymes, and subsequently with an acidic aqueous solution followed by a separation step to remove internal soluble cell constituents, wherein the yeast is not treated with alkali, thereby generating a coating agent consisting essentially of cell residue of yeast; and coating the surface of a solid material with the coating agent to form a continuous, low oxygen or gas permeable coating thereon.

11. A method for producing a coating agent, comprising treating a yeast cell by autolysis, or with external enzymes selected from the group consisting of proteases, nuclease, β-glucanase, esterases, lipases and combinations thereof, or with a combination of autolysis and one or more of the external enzymes, and subsequently with an acidic aqueous solution followed by a separation step to remove internal soluble cell constituents, wherein the yeast is not treated with alkali, thereby producing a coating agent that can form a continuous, low oxygen or gas permeable film coating a solid material.

12. A method for producing a coated material, comprising coating the surface of a solid material with a coating agent, wherein the coating agent comprises yeast cell wall fractions that consist essentially of cell residue of yeast from which internal soluble cell constituents have been removed by treating yeast cells by autolysis, or with external enzymes selected from the group consisting of proteases, nuclease, β-glucanase, esterases, lipases and combinations thereof, or with a combination of autolysis and one or more of the external enzymes, and subsequently with an acidic aqueous solution followed by a separation step, wherein the yeast have not been treated with alkali, thereby forming a continuous, low oxygen or gas permeable film coating the solid material.

* * * * *